(12) United States Patent
Gho et al.

(10) Patent No.: US 10,973,765 B2
(45) Date of Patent: Apr. 13, 2021

(54) CELL MEMBRANE-DERIVED NANOVESICLES AND USE THEREOF

(71) Applicant: POSTECH ACADEMY-INDUSTRY FOUNDATION, Pohang-si (KR)

(72) Inventors: Yong Song Gho, Pohang-si (KR); Dong-Sic Choi, Pohang-si (KR); Gyeongyun Go, Pohang-si (KR)

(73) Assignee: POSTECH ACADEMY-INDUSTRY FOUNDATION, Pohang-si (KR)

( * ) Notice: Subject to any disclaimer, the term of this patent is extended or adjusted under 35 U.S.C. 154(b) by 0 days.

(21) Appl. No.: 15/545,398

(22) PCT Filed: Aug. 24, 2015

(86) PCT No.: PCT/KR2015/008801
§ 371 (c)(1),
(2) Date: Nov. 1, 2017

(87) PCT Pub. No.: WO2016/133254
PCT Pub. Date: Aug. 25, 2016

(65) Prior Publication Data
US 2018/0036240 A1    Feb. 8, 2018

(30) Foreign Application Priority Data
Jan. 29, 2015  (KR) .......... 10-2015-0014164

(51) Int. Cl.
| | | |
|---|---|---|
| A61K 51/00 | (2006.01) | |
| A01N 25/26 | (2006.01) | |
| A61K 9/127 | (2006.01) | |
| A61K 48/00 | (2006.01) | |
| A61K 49/00 | (2006.01) | |
| A61K 47/50 | (2017.01) | |
| A61K 9/51 | (2006.01) | |
| A61K 9/50 | (2006.01) | |
| A61K 31/704 | (2006.01) | |
| A61K 31/713 | (2006.01) | |
| A61K 33/26 | (2006.01) | |
| A61K 38/46 | (2006.01) | |

(52) U.S. Cl.
CPC .......... *A61K 9/1273* (2013.01); *A61K 9/5068* (2013.01); *A61K 9/5089* (2013.01); *A61K 9/5192* (2013.01); *A61K 31/704* (2013.01); *A61K 31/713* (2013.01); *A61K 33/26* (2013.01); *A61K 38/465* (2013.01); *A61K 47/50* (2017.08); *A61K 48/00* (2013.01); *A61K 49/00* (2013.01); *A61K 49/0067* (2013.01); *A61K 49/0086* (2013.01); *C12Y 301/27005* (2013.01)

(58) Field of Classification Search
CPC .... A61K 9/1273; A61K 9/5068; A61K 48/00; A61K 49/0086
USPC ....................... 424/1.21, 417, 450
See application file for complete search history.

(56) References Cited

U.S. PATENT DOCUMENTS

2008/0268429 A1    10/2008    Pietrzkowski
2013/0302856 A1    11/2013    Yoo et al.

FOREIGN PATENT DOCUMENTS

| EP | 2 450 032 A2 * | 5/2012 |
| KR | 10-2011-0002443 | 1/2011 |
| WO | 2009-130649 | 10/2009 |

OTHER PUBLICATIONS

Bolton et al., 2006, US 20060035809 A1.*
Fujiki, Yukio et aL, "Isolation of intracellular Membranes by Means of Sodium Carbonate Treatment: Application to Endoplasmic Reticulum", The Journal of Cell Biology, 1982, vol. 93, No. L pp. 97-102.

* cited by examiner

*Primary Examiner* — Shin Lin Chen
(74) *Attorney, Agent, or Firm* — Lex IP Meister, PLLC

(57) ABSTRACT

Disclosed are cell membrane-derived nanovesicles, a method of preparing the nanovesicles, and a pharmaceutical composition and a diagnostic kit using the nanovesicles. The cell membrane-derived nanovesicles may prevent potential adverse effects because intracellular materials (e.g., genetic materials and cytosolic proteins) unnecessary for delivering therapeutic or diagnostic substances are removed from the nanovesicles. In addition, as the nanovesicles may be targeted to specific cells or tissues, therapeutic or diagnostic substances may be predominantly delivered to the targeted cells or tissues, while delivery of the substances may be inhibited. Therefore, the nanovesicles may alleviate suffering and inconvenience of patients by reducing adverse effects of therapeutic substances and by improving efficacy of the substances. In addition, the cell membrane-derived nanovesicles loaded with therapeutic or diagnostic substances and a method of preparing the nanovesicles may be used in vitro or in vivo for therapeutic or diagnostic purposes, or for experimental use.

5 Claims, 15 Drawing Sheets

• Bar, 100 nm

FIG. 5

| G. protein (GAPDH) | RT-PCR | | PCR | |
|---|---|---|---|---|
| DNase treatment | DNase (-) | DNase (+) | DNase (-) | DNase (+) |
| U937 cell (1 × 10⁶ cells) | 29.9 ± 0.2 | 31.0 ± 0.0 | 33.8 ± 0.1 | 40.0 ± 0.0 |
| U937 MNV (100 ng in proteins) | 40.0 ± 0.0 | 40.0 ± 0.0 | 40.0 ± 0.0 | 40.0 ± 0.0 |

| | Ct value | |
|---|---|---|
| | Actin | GAPDH |
| U937 cells | 31.59 ± 0.17 | 31.44 ± 0.34 |
| U937NV | 32.63 ± 0.03 | 33.42 ± 0.15 |
| U937EXO | 31.38 ± 0.15 | 32.23 ± 0.07 |

CELL MEMBRANE-DERIVED NANOVESICLES AND USE THEREOF

STATEMENT REGARDING GOVERNMENT RIGHTS

The present invention was undertaken with the support of Studies on the mechanisms of bacterial exosome-mediated tumor metastasis No. 2015R1A2A1A10055961 grant funded by the Ministry of Science ICT and Future Planning.

CROSS-REFERENCE TO RELATED APPLICATION

This application claims priority to and the benefit of Korean Patent Application No. 10-2015-0014164, filed on Jan. 29, 2015 and International Patent Application No. PCT/KR2015/008801, filed on Aug. 24, 2015, the disclosure of which is incorporated herein by reference in its entirety.

TECHNICAL FIELD

The present invention relates to cell membrane-derived nanovesicles, a method of preparing the same, and a pharmaceutical composition and a diagnostic kit using the nanovesicles.

BACKGROUND ART

When a drug is administered to an individual for disease treatment, a drug delivery system (DDS) that controls the delivery and release of the administered drug into cells, tissues, and organs for optimal efficacy is important. The drug delivery system is used to maintain adequate blood concentrations of a drug to achieve the maximum therapeutic effect. When the drug delivery system is applied, advantages such as maximizing the efficacy and stability of a drug, prolonging the residence time of a drug, increasing the bioavailability of a drug, and minimizing the side effects of a drug can be achieved. Thus, the drug delivery system is a medical technique required to efficiently deliver a drug to specific body parts and is considered as important as medicine itself. Since the early 1960s, drug delivery systems have been developed in the forms of injection and infusion, in the form of suppositories, for nasal and oral administration, and for administration via the skin or the lungs. In recent years, various drug delivery systems (DDSs), such as absorption-promoting and controlled DDSs (oral, transdermal, mucosal), sustained DDSs (injections, oral, transdermal), targeted DDSs (oral, injections, etc.), and artificial intelligence (intelligent) DDSs (on-demand type), have been developed and applied differently according to patients and purpose of use.

Among DDSs, liposomes have been widely studied as a drug delivery system since liposomes were first used in the 1960s. Liposomes are artificial membranes similar to cell membranes made of various phospholipids, and can be seen as colloidal semi-solid dispersants with a nanoscale particle size. Liposomal preparations have low toxicity and are highly applicable because the size, charge, membrane composition, and membrane permeability of the liposomal preparations may be controlled according to prescription. Recently, stealth liposomes prepared by conjugating liposomes with a polymer such as polyethylene glycol (PEG) have been developed. The stealth liposomes increase the circulatory half-life of drugs by preventing drug-containing liposomes from being easily removed from the blood. Using this method, DOXIL that delivers doxorubicin, an anticancer agent, has been commercialized. However, since liposomes and stealth liposomes lack the ability to recognize specific types of cells, the liposomes and stealth liposomes may not be used for the purpose of delivering drugs to specific types of cells or tissues. To enable liposomes to bind to specific targets, liposomes conjugated with antibodies specific to a single target have been developed, but none have been commercialized after passing clinical trials.

Therefore, a delivery system using natural cell membranes instead of liposomes made of artificially synthesized lipids is being developed. Since cell-derived delivery systems utilize the natural targeting systems of the cells, unlike conventional delivery systems such as liposomes, targeting may be easily induced. As a representative example, studies on drug delivery using extracellular vesicles which are naturally secreted from cells are underway. In addition, studies have been reported on loading various drugs, such as anticancer drugs, into nanovesicles (microvesicles) artificially prepared from nucleated mammalian cells and delivering the nanovesicles to cancer tissues.

In addition to substances required for their targeting, however, the extracellular vesicles and the nanovesicles artificially prepared from cells include intracellular components, such as cytosolic proteins and genetic materials (DNA and RNA), which are unnecessary for targeting. The components unnecessary for their targeting have a potential to lower the efficiency of drug loading or to induce side effects when administered into the body, and thus development of systems that are lacking their intraluminal components is essential.

DISCLOSURE

Technical Problem

The present inventors have conducted studies for solving the conventional problems as described above. As a result, the inventors have found that, when cells are treated with an alkaline solution of pH 9 to 14, the membranes of the cells from which intracellular components, such as genetic materials and cytosolic proteins, are removed may be selectively extracted and that nanovesicles may be prepared using these extracted cell membranes. Thus, the present invention was completed.

Accordingly, the present invention is directed to providing nanovesicles, wherein the nanovesicles are derived from the membranes of cells, the intracellular components of which have been removed by treating the cells with an alkaline solution of pH 9 to 14, and the size of the nanovesicles is smaller than that of the cells, and a method of delivering drugs using the same.

It is another object of the present invention to provide a method of preparing cell membrane-derived nanovesicles loaded with substances for treating or diagnosing diseases.

However, the technical problems to be solved by the present invention are not limited to the above-mentioned problems, and other problems not mentioned can be clearly understood by those skilled in the art from the following description.

Technical Solution

One aspect of the present invention provides nanovesicles, wherein the nanovesicles are derived from the membranes of cells, the intracellular components of which have been removed by treating the cells with an alkaline solution of pH 9 to 14, and the size of the nanovesicles is smaller than that of the cells.

In one embodiment of the present invention, the alkaline solution may be prepared using one or more selected from the group consisting of sodium carbonate ($Na_2CO_3$), sodium hydroxide (NaOH), ammonia ($NH_3$), calcium hydroxide ($Ca(OH)_2$), potassium hydroxide (KOH), sodium hydrogen carbonate ($NaHCO_3$), and magnesium hydroxide ($Mg(OH)_2$).

In another embodiment of the present invention, the cells may be selected from the group consisting of monocytes, macrophages, dendritic cells, and stem cells as nucleated mammalian cells.

In another embodiment of the present invention, the cells may be transformed cells that target specific types of cells or tissues.

In another embodiment of the present invention, the cells may be transformed cells that express one or more selected from the group consisting of cell adhesion molecules, antibodies, targeting proteins, cell membrane fusion proteins, and fusion proteins thereof.

In another embodiment of the present invention, the cells may be transformed cells that express one or more selected from the group consisting of growth factors, cytokines, receptors, fluorescent proteins, and fusion proteins thereof.

In another embodiment of the present invention, the membranes of the nanovesicles may further include a component other than the membranes of the cells.

In another embodiment of the present invention, the component other than the cell membrane may be cyclodextrin or polyethylene glycol.

In another embodiment of the present invention, the nanovesicles may have a chemically modified membrane component.

In another embodiment of the present invention, the nanovesicles may retain the topology of the membrane proteins of the cells from which the nanovesicles originated.

Another aspect of the present invention provides a pharmaceutical composition for delivering substances, including the nanovesicles loaded with substances for treating or diagnosing diseases.

In one embodiment of the present invention, the substances for treating or diagnosing diseases may be injected.

In another embodiment of the present invention, the substances for treating or diagnosing diseases may be one or more selected from the group consisting of anti-cancer agents, anti-inflammatory agents, angiogenesis inhibitors, peptides, proteins, toxins, nucleic acids, beads, microparticles, and nanoparticles.

In another embodiment of the present invention, the nucleic acids may be selected from the group consisting of DNA, RNA, aptamers, locked nucleic acids (LNAs), peptide nucleic acids (PNAs), and morpholinos.

In another embodiment of the present invention, the nanoparticles may be selected from the group consisting of iron oxides, gold, carbon nanotubes, and magnetic beads.

In another embodiment of the present invention, the substances for treating or diagnosing diseases may be fluorescence-emitting materials.

In another embodiment of the present invention, the fluorescence-emitting materials may be fluorescent proteins or quantum dots.

Still another aspect of the present invention provides a method of preparing cell membrane-derived nanovesicles loaded with substances for treating or diagnosing diseases, the method including the following steps:

(a) a step of removing intracellular materials by treating cells with an alkaline solution of pH 9 to 14;

(b) a step of adding therapeutic or diagnostic substances into a suspension containing the membranes of the cells from which the intracellular materials have been removed;

(c) a step of preparing nanovesicles by applying a sonication method to the suspension to which the therapeutic or diagnostic substances are added; and (d) a step of separating the prepared nanovesicles from the suspension.

Yet another aspect of the present invention provides a method of preparing cell membrane-derived nanovesicles loaded with substances for treating or diagnosing diseases, the method including the following steps:

(a) a step of removing intracellular materials by treating cells with an alkaline solution of pH 9 to 14;

(b) a step of preparing nanovesicles by applying a sonication method to a suspension containing the membranes of the cells from which the intracellular materials have been removed;

(c) a step of adding therapeutic or diagnostic substances into the suspension containing the nanovesicles and incubating the mixture; and (d) a step of separating the incubated nanovesicles from the suspension.

In one embodiment of the present invention, the method may further include a step of extruding the nanovesicles prepared by the sonication method.

In another embodiment of the present invention, the alkaline solution may be prepared using one or more selected from the group consisting of sodium carbonate ($Na_2CO_3$), sodium hydroxide (NaOH), ammonia ($NH_3$), calcium hydroxide ($Ca(OH)_2$), potassium hydroxide (KOH), sodium hydrogen carbonate ($NaHCO_3$), and magnesium hydroxide ($Mg(OH)_2$).

In another embodiment of the present invention, the cells may be selected from the group consisting of monocytes, macrophages, dendritic cells, and stem cells as nucleated mammalian cells.

In another embodiment of the present invention, the cells may be transformed cells that target specific types of cells or tissues.

In another embodiment of the present invention, the cells may be transformed cells that express one or more selected from the group consisting of cell adhesion molecules, antibodies, targeting proteins, cell membrane fusion proteins, and fusion proteins thereof.

In another embodiment of the present invention, the cells may be transformed cells that express one or more selected from the group consisting of growth factors, cytokines, receptors, fluorescent proteins, and fusion proteins thereof.

In another embodiment of the present invention, the membranes of the nanovesicles may further include a component other than the membranes of the cells.

In another embodiment of the present invention, the component other than the cell membrane may be cyclodextrin or polyethylene glycol.

In another embodiment of the present invention, the nanovesicles may have a chemically modified membrane component.

In another embodiment of the present invention, the nanovesicles may retain the topology of the membrane proteins of the cells from which the nanovesicles originated.

In another embodiment of the present invention, the therapeutic or diagnostic substances may be injected from outside the cells.

In another embodiment of the present invention, the substances for treating or diagnosing diseases may be one or more selected from the group consisting of anti-cancer agents, anti-inflammatory agents, angiogenesis inhibitors, peptides, proteins, toxins, nucleic acids, beads, microparticles, and nanoparticles.

In another embodiment of the present invention, the nucleic acids may be selected from the group consisting of DNA, RNA, aptamers, locked nucleic acids (LNAs), peptide nucleic acids (PNAs), and morpholinos.

In another embodiment of the present invention, the nanoparticles may be selected from the group consisting of iron oxides, gold, carbon nanotubes, and magnetic beads.

In another embodiment of the present invention, the substances for treating or diagnosing diseases may be fluorescence-emitting materials.

In another embodiment of the present invention, the fluorescence-emitting materials may be fluorescent proteins or quantum dots.

Yet another aspect of the present invention provides a composition for diagnosing diseases, including the nanovesicles of the present invention loaded with primers, probes, antisense nucleic acids, or antibodies required for diagnosis of diseases.

Yet another aspect of the present invention provides a kit for diagnosing diseases, including the composition of the present invention.

Yet another aspect of the present invention provides a method of delivering substances, the method including a step of delivering therapeutic or diagnostic substances into the specific types of cells or tissues using the nanovesicles of the present invention.

Yet another aspect of the present invention provides a method of treating or diagnosing diseases, the method including a step of delivering therapeutic or diagnostic substances into the specific types of cells or tissues using the nanovesicles of the present invention Yet another aspect of the present invention provides a therapeutic or diagnostic use of the nanovesicles of the present invention.

Advantageous Effects

The cell membrane-derived nanovesicles according to the present invention can prevent the occurrence of potential side effects because intracellular or intraluminal materials (e.g., genetic materials and cytosolic proteins) unnecessary for delivery of therapeutic or diagnostic substances are removed from the extracellular vesicles and artificial nanovesicles. In addition, since the nanovesicles can be targeted to the specific types of cells or tissues, therapeutic or diagnostic substances may be predominantly delivered to the targeted cells or tissues while delivery of therapeutic or diagnostic substances to untargeted sites may be inhibited. Therefore, when the cell membrane-derived nanovesicles are applied to disease treatment, the side effects of therapeutic substances such as drugs can be reduced, so that suffering and inconvenience of patients can be alleviated during the course of treating diseases, and therapeutic efficacy can be improved. In addition, the cell membrane-derived nanovesicles of the present invention, in which substances for the treatment or diagnosis of diseases are loaded, and a method of preparing the nanovesicles can be used in vitro or in vivo for therapeutic or diagnostic purposes, or for experimental use.

DESCRIPTION OF DRAWINGS

FIG. 5 shows the results of real-time RT-PCR and RT-PCR confirming that DNA and RNA are not present in nanovesicles derived from nucleated mammalian cells.

MODES OF THE INVENTION

Figure 1:
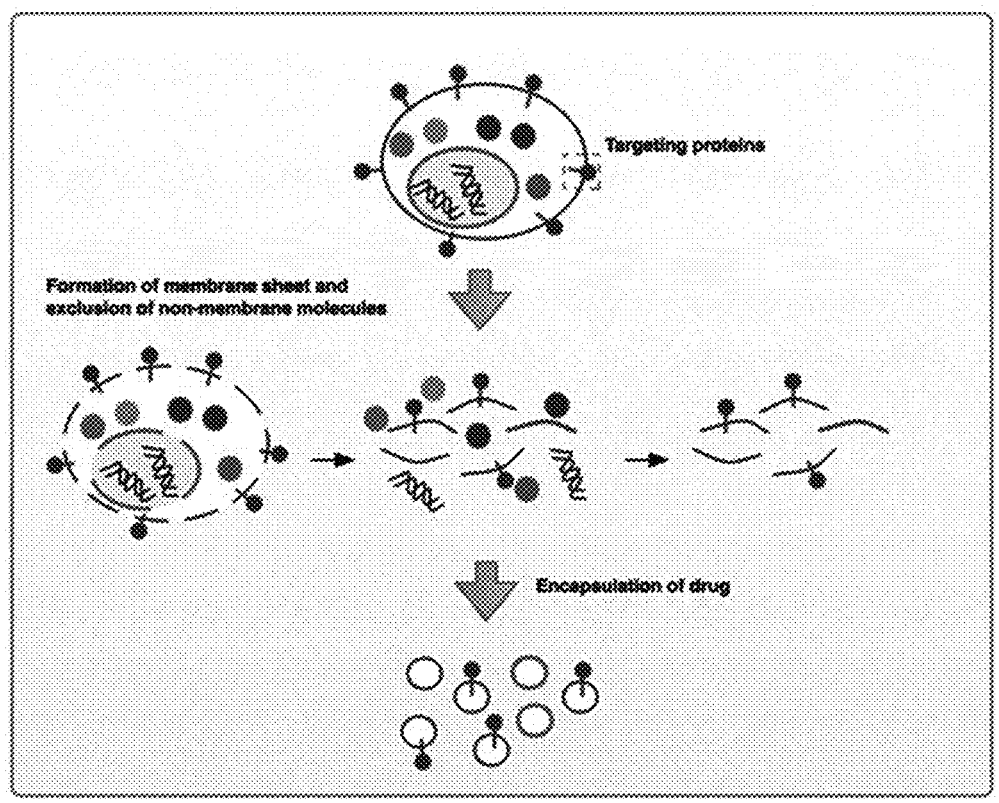
FIG. 1 illustrates nanovesicles derived from nucleated mammalian cells or transformed nucleated mammalian cells and shows a schematic diagram of a method of preparing the nanovesicles loaded with various substances, such as targeting substances and therapeutic and diagnostic substances.

The present invention provides nanovesicles, wherein the nanovesicles are derived from the membranes of cells, the intracellular components of which have been removed by treating the cells with an alkaline solution of pH 9 to 14, and the size of the nanovesicles is smaller than that of the cells.

The inside and outside of the nanovesicles of the present invention are distinguished by a lipid bilayer membrane composed of the cell membrane components of an originating cell. These nanovesicles include cell membrane lipids and proteins of the originating cells and have the same topologies as the originating cells. However, intracellular materials, such as genetic material (e.g., nucleic acids) and cytosolic proteins, are removed from the nanovesicles, and the size of the nanovesicles may be smaller than that of the originating cell, without being limited thereto.

The alkaline solution of the present invention may be prepared using one or more selected from the group consisting of sodium carbonate ($Na_2CO_3$), sodium hydroxide (NaOH), ammonia ($NH_3$), calcium hydroxide ($Ca(OH)_2$), potassium hydroxide (KOH), sodium hydrogen carbonate ($NaHCO_3$), and magnesium hydroxide ($Mg(OH)_2$), without being limited thereto.

The cells of the present invention may be selected from the group consisting of monocytes, macrophages, dendritic cells, and stem cells as nucleated mammalian cells, and may be also selected from the group consisting of cells differentiated from stem cells, and in particular, may include transformed cells that target specific types of cells or tissues. Specifically, the transformed cells may include various types of cells, which are transformed to express therapeutic and diagnostic substances, targeting substances, or substances necessary for cell membrane fusion with target cells, and the transformed cells may include a combination of two or more of the above cell types, without being limited thereto.

The nucleated mammalian cells may be transformed by material treatment or gene introduction, transformed more than once, and transformed to inhibit the expression of one or more specific proteins.

As used herein, the term, "transformation" refers to a method of increasing or decreasing the expression of substances such as proteins by stimulating cells and a method of changing the expression of proteins by gene introduction, and methods commonly used in the art may be used. As methods of increasing or inhibiting the expression of specific proteins by gene introduction, RNA interference (RNAi), virus-mediated methods, calcium phosphate precipitation, liposomes, electroporation, microinjection, ultrasound-mediated methods, and the like may be exemplified, and all generally known methods may be used.

The cells of the present invention may be transformed cells that express one or more selected from the group consisting of cell adhesion molecules, antibodies, targeting proteins, cell membrane fusion proteins, and fusion proteins thereof, and may be also transformed cells that express one or more selected from the group consisting of growth factors, cytokines, receptors, fluorescent proteins, and fusion proteins thereof, without being limited thereto.

The membranes of the nanovesicles of the present invention may include targeting substances, substances necessary for cell membrane fusion with target cells (e.g., fusogen), cyclodextrin, polyethylene glycol, and the like in addition to the cell membranes of originating cells, and the components other than the cell membranes may be added by various methods, including chemical modification of the cell membranes.

In addition, the present invention provides a pharmaceutical composition for delivering substances, including the nanovesicles loaded with substances for treating or diagnosing diseases.

According to the present invention, the nanovesicles may be prepared in various sizes depending on tissues targeted by diagnostic or therapeutic substances, and the size of the nanovesicles is preferably 10 nm or more and 10 µm or less.

Substances to be loaded into the nanovesicles of the present invention are not particularly limited, and may be therapeutic or diagnostic substances. In addition, substances prepared outside cells may be loaded, and the loaded substances may number one or more.

The substances for treating or diagnosing diseases may be one or more selected from the group consisting of anti-cancer agents, anti-inflammatory agents, angiogenesis inhibitors, peptides, proteins, toxins, nucleic acids, beads, microparticles, and nanoparticles, without being limited thereto.

The nucleic acids may be selected from the group consisting of DNA, RNA, aptamers, locked nucleic acids (LNAs), peptide nucleic acids (PNAs), and morpholinos, and the nanoparticles may be selected from the group consisting of iron oxides, gold, carbon nanotubes, and magnetic beads, without being limited thereto.

The substances for treating or diagnosing diseases according to the present invention may be fluorescence-emitting materials, preferably fluorescent proteins or quantum dots, without being limited thereto.

The pharmaceutical composition of the present invention may contain one or more of anti-cancer agents, anti-inflammatory agents, angiogenesis inhibitors, peptides, proteins, toxins, nucleic acids, beads, microparticles or nanoparticles as active ingredients. In addition, the pharmaceutical composition may be mixed with pharmaceutically acceptable carriers such as saline, sterilized water, Ringer's solution, buffered saline, cyclodextrin, a dextrose solution, a maltodextrin solution, glycerol, ethanol, liposomes and one or more of these carriers, and the pharmaceutical composition may further contain other conventional additives such as antioxidants, buffers, and the like, when desired. In addition, diluents, dispersants, surfactants, binders, or lubricants may be additionally added to the pharmaceutical composition, and thus the pharmaceutical composition may be formulated into injectable formulations, such as aqueous solutions, suspensions and emulsions, pills, capsules, granules or tablets. Furthermore, the pharmaceutical composition may be suitably formulated according to each component using appropriate methods in the art or methods disclosed in the Remington's reference (Remington's Pharmaceutical Science, Mack Publishing Company, Easton Pa.). The pharmaceutical composition of the present invention is not particularly limited in formulation, but is preferably formulated as an injection or an inhalant.

The method of administering the pharmaceutical composition of the present invention is not particularly limited, but the pharmaceutical composition may be administered parenterally, such as intravenously, subcutaneously, intraperitoneally, by inhalation or topical application, or orally, depending on the purpose. The dosage may be variously determined depending on a patient's body weight, age, sex, health condition, diet, administration time, administration methods, excretion amount and severity of diseases. Daily dose refers to the amount of a therapeutic substance capable of alleviating disease status upon administration of the therapeutic substance to an individual in need of treatment. The effective amount of the therapeutic substance depends on particular compounds, disease status and disease severity, individuals in need of treatment, which may be routinely determined by those of ordinary skill in the art. As a non-limiting example, the dosage of the composition of the present invention to human body may be varied depending on the patient's age, weight, sex, dosage form, health condition and disease severity. On the basis of an adult patient weighing 70 kg, the dose is generally 0.1 to 1,000 mg/day, preferably 1 to 500 mg/day. The composition may also be administered dividedly once or several times a day at regular time intervals.

In addition, the present invention provides a method of preparing cell membrane-derived nanovesicles loaded with substances for treating or diagnosing diseases, the method including a step of removing intracellular materials by treating cells with an alkaline solution of pH 9 to 14; a step of adding therapeutic or diagnostic substances into a suspension containing the membranes of the cells from which the intracellular materials have been removed; a step of preparing nanovesicles by applying a sonication method to the suspension to which the therapeutic or diagnostic substances are added; and a step of separating the prepared nanovesicles from the suspension.

In addition, the present invention provides a method of preparing cell membrane-derived nanovesicles loaded with substances for treating or diagnosing diseases, the method including a step of removing intracellular materials by treating cells with an alkaline solution of pH 9 to 14; a step of preparing nanovesicles by applying a sonication method to a suspension containing the membranes of the cells from which the intracellular materials have been removed; a step of adding therapeutic or diagnostic substances into the suspension containing the nanovesicles and incubating the mixture; and a step of separating the incubated nanovesicles from the suspension.

The method of the present invention may further include a step of extruding the nanovesicles prepared by the sonication method.

In the present invention, nanovesicles were prepared from a monocyte cell line, U937, and transformed HEK293 and HT1080 cells using the method of preparing the nanovesicles, i.e., using alkaline solution treatment, sonication, and a density gradient method (see Example 1).

In one embodiment of the present invention, when the shape and size of nanovesicles prepared from monocytes and transformed cells were determined, the nanovesicles were in the form of a spherical lipid bilayer, and monocyte-derived nanovesicles exhibited a size of 100 to 200 nm, i.e., 180 nm on average, while transformed cell-derived nanovesicles exhibited a size of 70 to 150 nm, i.e., 100 nm on average.

In addition, when western blotting was performed on the monocyte-derived nanovesicles and monocyte cells to determine the expression levels of β-actin (cytoplasmic protein), H2B (nucleoprotein), GM130, LFA1 and ICAM1 (cell membrane proteins), the nanovesicles did not contain cytoplasmic proteins and nucleoproteins, while cell membrane proteins were expressed in the nanovesicles. In addition, as a result of real-time PCR, it was confirmed that the nanovesicles do not contain DNA and RNA, i.e., nucleic acids, unlike monocyte cells. As a result of analyzing of the topology of the nanovesicles, the membrane proteins of the nanovesicles were located outside the nanovesicles, like the membrane proteins of monocyte cells. That is, the membrane proteins of the nanovesicles maintained the same topology as the membrane proteins of the monocyte cells (see Example 2).

In another embodiment of the present invention, nanovesicles containing polyethylene glycol were prepared by adding cholesterol-polyethylene glycol-biotin to the monocyte-derived nanovesicles prepared according to the method of Example 1. Thereafter, streptavidin-HRP was added to the nanovesicles, followed by incubation. After incubation, BM-POD as a substrate was added thereto to measure the amount of color development. As a result, it was confirmed that cholesterol-polyethylene glycol-biotin was bound to the nanovesicles containing polyethylene glycol (see Example 3).

In another embodiment of the present invention, when the nanovesicles were prepared using alkaline solution treatment, sonication, and a density gradient method according to the method of Example 1, in the step of performing sonication, FITC-siRNA, Qdot 705, or iron oxide nanoparticles were each loaded into nanovesicles, and the nanovesicles containing each of FITC-siRNA, Qdot 705, or iron oxide nanoparticles were prepared. After the preparation, it was inspected whether each substance was appropriately loaded into the nanovesicles. Fluorescence microscopy observation revealed that each of FITC-siRNA and Qdot 705 was properly loaded into nanovesicles. In addition, the density gradient method using an Optiprep solution confirmed that iron oxide nanoparticles were also loaded into nanovesicles (see Examples 4 to 6).

In another embodiment of the present invention, it was demonstrated that drug delivery at the cellular level and cell-specific drug delivery are possible when monocyte-derived nanovesicles are used. Monocyte-derived nanovesicles loaded with doxorubicin as a chemical drug or ribonuclease A (RNase A) as a protein drug were prepared. Thereafter, human umbilical vein endothelial cells (HUVECs), a human blood vessel cell line, were treated with TNF-α to activate the HUVECs, resulting in increased expression of cell adhesion molecules such as ICAM-1, VCAM-1, and E-selectin in cell membranes. It was confirmed whether the monocyte-derived nanovesicles recognize these molecules and the drugs are delivered to target cells. As a result, when TNF-α was treated, both doxorubicin and RNase A were delivered to HUVECs and induced cell death depending on the treatment concentration of the nanovesicles (see Example 7).

In another embodiment of the present invention, the drug delivery capacity of transformed cell-derived nanovesicles was verified at the cellular level. After nanovesicles loaded with doxorubicin or RNase were prepared from HT1080 transformed cells overexpressing ICAM1, U937 monocyte cells were treated with different concentrations of the prepared nanovesicles and incubated for 24 hours. After incubation, the monocyte cells were stained with a trypan blue solution to measure the degree of cell death. As a result, the drugs were delivered into the monocyte cells by the nanovesicles and in the case of monocyte cells were treated with doxorubicin-loaded nanovesicles, cell death was induced at a concentration of 5 μg/ml or more and in the case of RNase A, cell death was induced at a concentration of 10 μg/ml or more (see Example 8).

In another embodiment of the present invention, nanovesicles were prepared from transformed cells expressing adhesion molecules such as EGF and GE11 which were located in the membranes of the transformed cells and were capable of binding to EGFR expressed in the cell membranes of A549, a human lung cancer cell line. Then, the drug delivery capacity of the transformed cell-derived nanovesicles was confirmed. The nanovesicles loaded with doxorubicin were added to A549 cell-seeded plates and incubated. After incubation, the cells were observed under a fluorescence microscope. As a result, cell death was observed. Based on the result, it was confirmed that GE11 and EGF present in nanovesicles, which have been derived from transformed cells expressing EGF and GE11 in their cell membranes and loaded with anticancer drugs, may specifically bind to cells expressing EGFR on the cell surface and the loaded anticancer drugs may be delivered to cells to induce cell death (see Example 9).

In addition, the present invention provides a composition for diagnosing diseases, including the nanovesicles of the present invention loaded with primers, probes, antisense nucleic acids, or antibodies required for diagnosis of diseases.

In addition, the present invention provides a kit for diagnosing diseases, including the composition.

Hereinafter, preferred examples are described to facilitate understanding of the present invention. However, the following examples are provided only for the purpose of easier understanding of the present invention, and the present invention is not limited by the following examples.

EXAMPLES

Example 1

Preparation of Nanovesicles by Alkaline Solution Treatment and Sonication

To prepare nanovesicles derived from nucleated mammalian cells or transformed nucleated mammalian cells from which intracellular components had been removed, monocytes or transformed cells were subjected to alkaline solution treatment, sonication, and a density gradient method, and a schematic diagram for preparing the nanovesicles is shown in FIG. 1.

$8 \times 10^7$ U937 cells (ATCC No. CRL-1593.2) were used as monocytes and $4 \times 10^7$ HEK293 cells (ATCC No. CRL-1573) or $4 \times 10^7$ HT1080 cells (ATCC No. CCL-121) were used as transformed cells. Each cell type was treated with 8 ml of an alkaline solution (200 mM $Na_2CO_3$, 1× phosphatase inhibitor, pH 11.5), the solution was sonicated 30 times with a sonicator under the conditions of cycle: 0.5 and amplitude: 50, and ultracentrifugation was performed at 100,000×g for 15 minutes to obtain a pellet. The pellet was resuspended in 8 ml of the alkaline solution, stored in a rotor set at 4° C. for 30 minutes, and was subjected to ultracentrifugation at 100,000×g for 15 minutes to obtain a pellet. The obtained pellet was resuspended with 10 ml of a HEPES buffered saline (HBS) solution, and was again subjected to ultracentrifugation at 100,000×g for 15 minutes to obtain a pellet. The pellet was suspended with 0.4 ml of a HBS solution, sonication was performed 30 times with a sonicator, sonication was performed again for 30 minutes in a water bath sonicator, and the solution was suspended with 6.6 ml of a HBS solution. Next, 1 ml of 50% Optiprep, 2 ml of 10% Optiprep, and 7 ml of the suspension were sequentially added into an 11 ml ultracentrifuge tube, and ultracentrifugation was performed at 100,000×g for 2 hours to obtain nanovesicles present in the layer between the 50% Optiprep and 10% Optiprep.

Example 2

Characterization of Nanovesicles 2-1. Identification of Shape and Size of Nanovesicles The shape and size of the monocyte- and transformed cell-derived nanovesicles prepared by the method of Example 1 were analyzed. First, the nanovesicles derived from monocytes were observed using a transmission electron microscope. The nanovesicles derived from monocytes were adsorbed in a glow-discharged carbon-coated copper grid for 3 minutes. The grid was washed with distilled water, stained with 2% uranyl acetate for 1 minute, and observed with JEM101 (Jeol, Japan), an electron microscope.

Figure 2A:
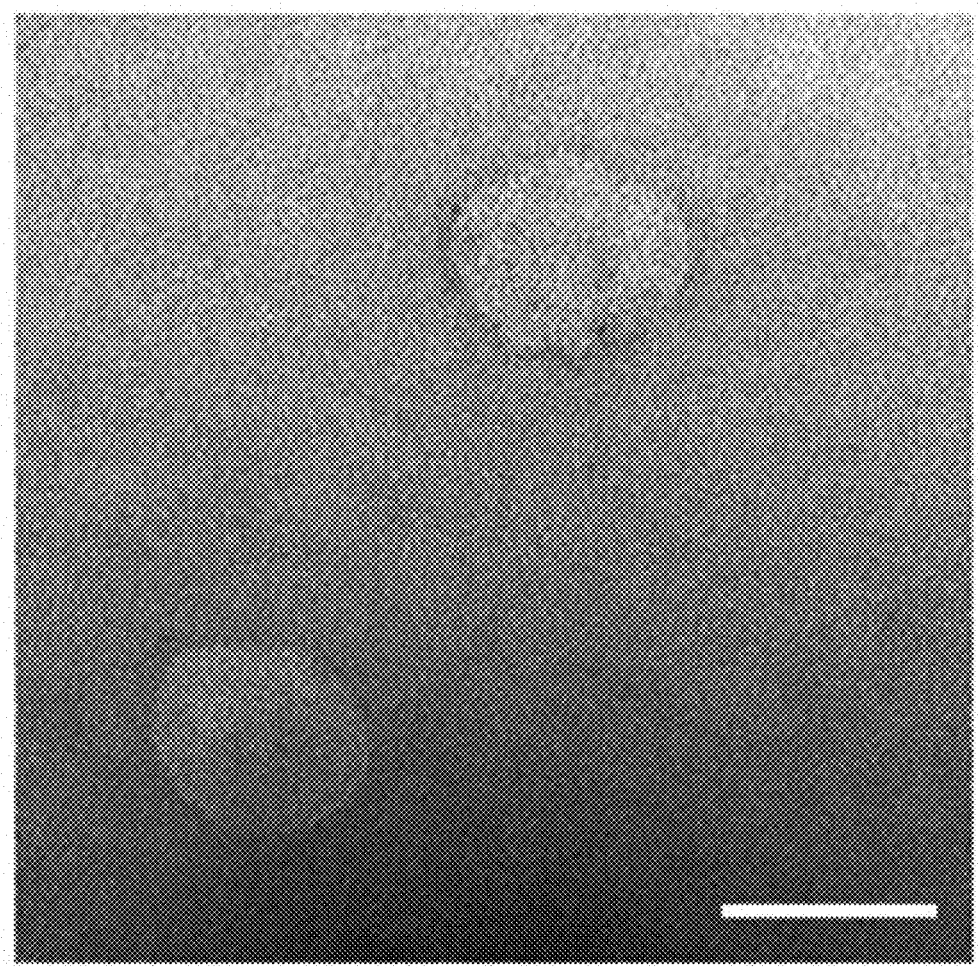
FIG. 2A shows a transmission electron microscope image of nanovesicles prepared from nucleated mammalian cells using alkaline solution treatment, sonication, and a density gradient method.
Figure 2B:
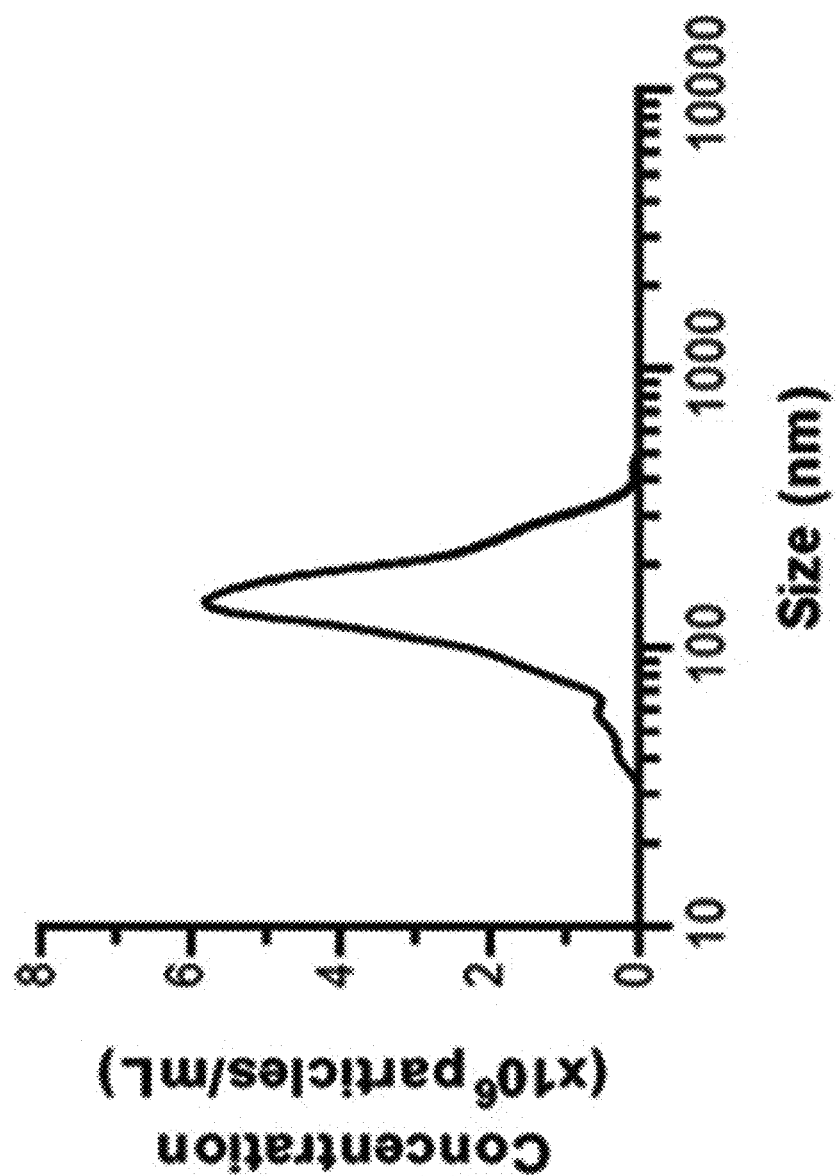
FIG. 2B is a graph showing the size of nanovesicles prepared from nucleated mammalian cells using alkaline solution treatment, sonication, and a density gradient method.

As a result, as shown in FIG. 2a, it was found that the nanovesicles prepared from monocytes using alkaline solution treatment were composed of lipid bilayers, had a size of 100 to 200 nm, and exhibited a generally spherical shape. In addition, the nanovesicles prepared from monocytes were diluted in 1 ml of HBS to a concentration of 0.5 µg/ml, 1 ml of the HBS solution containing the nanovesicles was placed in a chamber, and analyzed with a nanoparticle tracking analysis instrument. As shown in FIG. 2b, the size of the nanovesicles was 100 to 200 nm and the average size was 180 nm.

In addition, nanovesicles prepared from transformed cells expressing epidermal growth factor (EGF) and a GE11 peptide (YHWYGYTPQNVI) were diluted in 1 ml of HBS to a concentration of 5 µg/ml, 1 ml of the HBS containing the nanovesicles was added to a cuvette and analyzed with a dynamic light scattering instrument.

Figure 3:
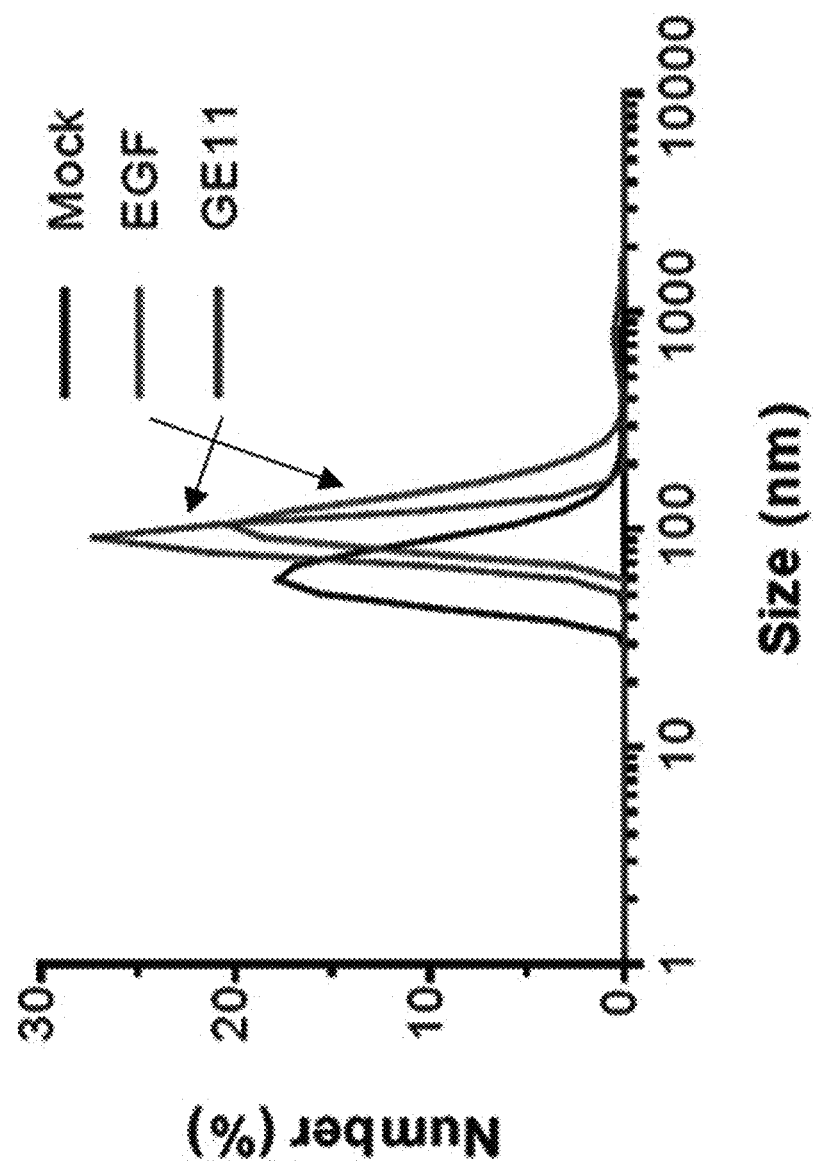
FIG. 3 is a graph showing the size of nanovesicles derived from transformed nucleated mammalian cells.

As a result, as shown in FIG. 3, the nanovesicles prepared from the transformed cells had a size of 70 to 150 nm, and the average size thereof was 100 nm.

2-2. Verification of Presence or Absence Of Cytoplasmic Proteins and Nucleoproteins in Monocyte-Derived Nanovesicles To determine whether nanovesicles prepared from monocytes using alkaline solution treatment according to the method of Example 1 contained cytoplasmic proteins and nucleoproteins, western blotting was performed on the nanovesicles and monocyte cells.

5 µg of each of the nanovesicles and the monocyte cells was prepared, 5× loading dye (250 mM Tris-HCl, 10% SDS, 0.5% bromophenol blue, 50% glycerol) was added thereto so as to be finally 1×, and then the mixture was treated at 100° C. for 5 minutes. A 12% polyacrylamide gel was prepared, samples were loaded onto the gel, and polyacrylamide gel electrophoresis was performed at 80 V for 2 hours. A transfer process was performed at 400 mA for 2 hours so that proteins on the gel were transferred onto a polyvinylidene fluoride (PVDF) membrane by electric current. After the transfer process was completed, a blocking process was performed by soaking the membrane in 0.05% TBS-T (Tween-20) containing 3% non-fat milk and incubating the membrane for 2 hours. After blocking, the membrane was treated with primary antibodies that specifically bind to the respective proteins of β-actin, H2B, GM130, LFA1, and ICAM1, followed by reaction at room temperature for 2 hours. After washing the membrane three times with 0.05% TBS-T (Tween-20), the membrane was treated with secondary antibodies conjugated with peroxidase, followed by reaction at room temperature for 90 minutes. Thereafter, the membrane was washed three times with 0.05% TBS-T (Tween-20), and then the expression of each protein was determined using enhanced chemiluminescence (ECL, Amersham Co. No. RPN2106), WEST-ZOL (iNtRON. No. 16024), or Femto (Thermo Scientific. No. 37074).

Figure 4:
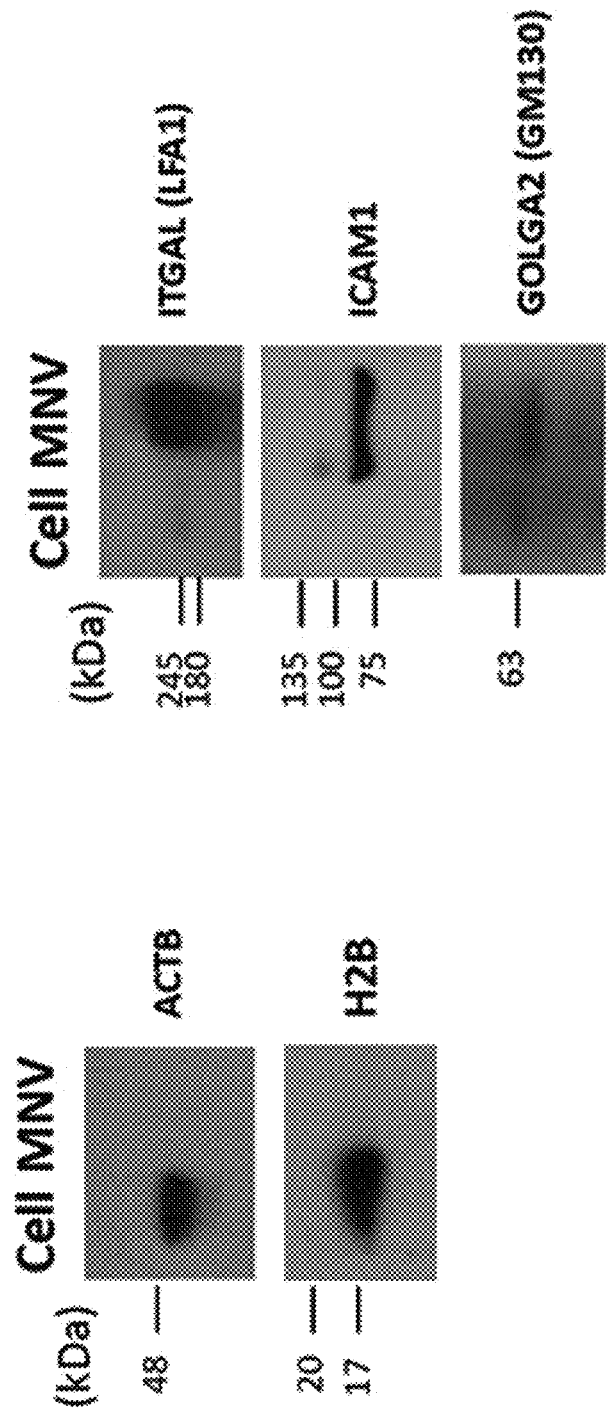
FIG. 4 shows western blotting results confirming that cytoplasmic proteins and nucleoproteins are absent in nanovesicles derived from nucleated cells and that a large amount of membrane proteins is present.

As shown in FIG. 4, monocyte cells expressed β-actin (ACTB), which is a main component of the cytoskeleton and present in the cytoplasm, and H2B, a protein constituting a histone in the nucleus, whereas nanovesicles (MNV) prepared using alkaline solution treatment did not express β-actin (ACTB) and H2B. In addition, compared with monocyte cells, nanovesicles prepared using alkaline solution treatment highly expressed cell membrane proteins such as LFA-1, ICAM1, and GM130. Based on the results, the nanovesicles prepared using alkaline treatment did not express cytoplasmic proteins and nucleoproteins, such as β-actin and H2B, whereas the nanovesicles contained more cell membrane proteins, such as LFA-1, ICAM1 and GM130, compared to cells.

2-3. Verification of Presence or Absence of Nucleic Acids in Monocyte-Derived Nanovesicles To determine whether the nanovesicles prepared from monocytes using alkaline solution treatment according to the method of Example 1 contained nucleic acids, real-time RT-PCR and real-time PCR were performed on the nanovesicles and monocyte cells.

100 ng of nanovesicles prepared from monocytes and 1×10$^5$ monocyte cells were incubated at 95° C. for 10 minutes. Consequently, the nanovesicles and the cells burst and all internal nucleic acids were released. Then, real-time RT-PCR and real-time PCR were performed to determine the expression level of GAPDH under conditions in which a DNA-degrading enzyme (e.g., DNase) was treated or not treated.

As shown in FIG. 5, to determine whether the nanovesicles prepared from monocytes contained nucleic acids, real-time RT-PCR was performed to measure the expression of GADPH without DNase treatment. As a result, nucleic acids were not present in the nanovesicles prepared from monocytes, whereas nucleic acids were present in the monocyte cells. To determine whether the nanovesicles contained RNA, the solution containing the burst nanovesicles or monocyte cells was treated with DNase to remove DNA, and then DNase inhibitors were added thereto to inhibit DNase activity. Real-time RT-PCR was performed using RNA as a template to measure the expression of GADPH. As a result, RNA was not present in the nanovesicles prepared from monocytes, whereas RNA was present in the monocyte cells. To determine whether the nanovesicles contained DNA, the solution containing the burst nanovesicles or monocyte cells were subjected to real-time PCR for GADPH without DNase treatment. As a result, DNA was not present in the nanovesicles prepared from monocytes whereas DNA was present in the monocyte cells. Furthermore, when real-time PCR for GADPH was performed on the solution containing the burst nanovesicles or monocyte cells after DNase treatment, DNA was not present in the monocyte cells either. This result indicated that DNase had enzymatic activity. These results indicated that DNA and RNA are both present in the monocyte cells, whereas DNA and RNA are not present in the nanovesicles derived from monocyte cells.

2-4. Topology Analysis of Nanovesicles

To analyze the topology of the nanovesicles prepared from monocytes, among alkaline solution treatment, sonication, and a density gradient method according to the method of Example 1, in the step of sonication, the nanovesicles were loaded with an enhanced green fluorescent protein (EGFP).

More specifically, when nanovesicles were prepared from U937 cells, monocytes, as shown in Example 1, the pellet was suspended with 10 ml of a HEPES buffered saline (HBS) solution, ultracentrifugation was performed at 100,000×g for 15 minutes to obtain a pellet. Then, the obtained pellet was suspended with HBS, EGFP was added to the HBS solution at a concentration of 50 μg/ml to prepare a solution with a final volume of 0.4 ml. The following procedures were performed in the same manner as Example 1, and monocyte-derived nanovesicles loaded with EGFP were obtained. 10 μg of EGFP-loaded nanovesicles and 30 ng of EGFP proteins were prepared and were not treated with or treated with 1 μg of trypsin at 37° C. for 4 hours to prepare trypsin-treated samples and trypsin-untreated samples. Western blotting was performed in the same manner as described in Example 2-2. ICAM1- or EGFP-specific antibodies were used as primary antibodies, and the '+' sign indicates treatment with trypsin, while the '−' sign indicates treatment without trypsin.

Figure 6:
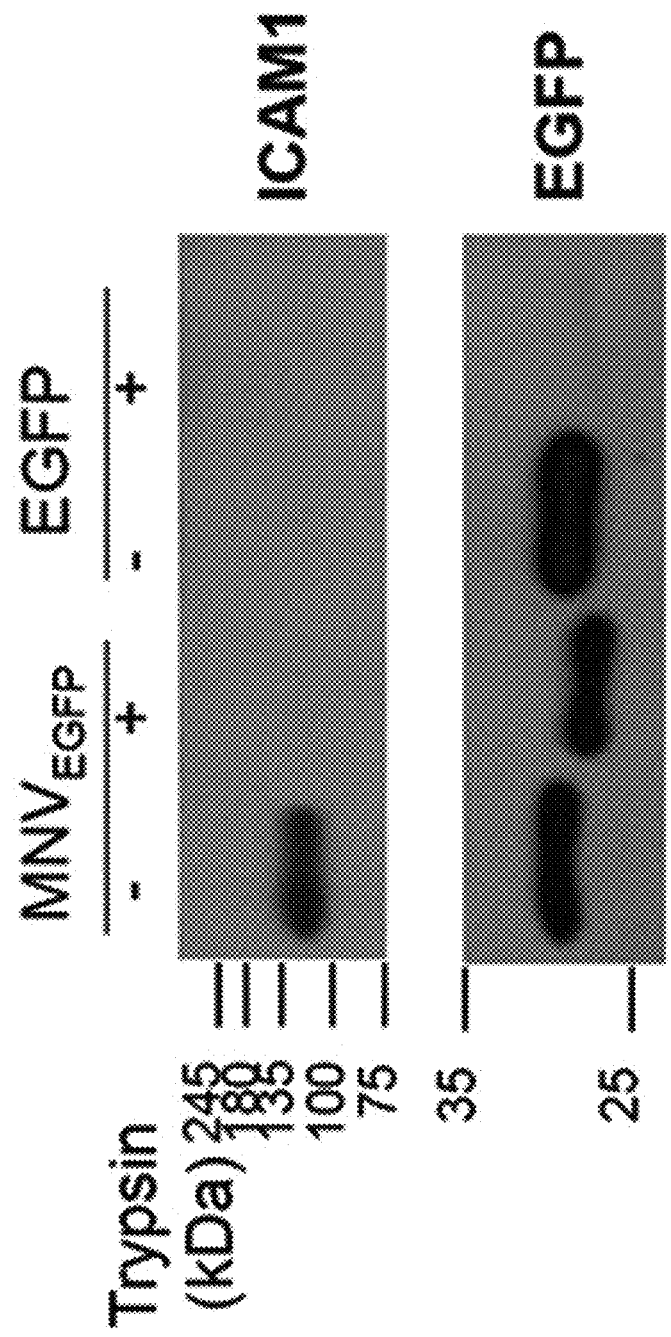
FIG. 6 shows that the topology of nanovesicles derived from nucleated mammalian cells is normal. This was confirmed by determining whether an ICAM1 protein of nanovesicles derived from nucleated mammalian cells and an EGFP protein loaded into the nanovesicles were expressed, after trypsin treatment.

As a result, as shown in FIG. 6, when trypsin was not treated, ICAM1 and EGFP proteins were detected in the case of nanovesicles (MNV$_{EGFP}$) and EGFP proteins were also detected in the case of EGFP. However, when trypsin was treated, in the case of EGFP, EGFP proteins were degraded by trypsin and thus EGFP proteins were not detected. On the other hand, in the case of the nanovesicles, the extracellular domain of ICAM1 was degraded and not detected, and EGFP proteins loaded into the nanovesicles were not degraded. When the inner and outer parts of the cell membrane are partially reversed and thereby the extracellular domain of ICAM1 is directed toward the inside of nanovesicles, the extracellular domain of ICAM1 is not degraded by trypsin, and thus an antibody reaction may be induced. In the nanovesicles treated with trypsin, an antibody reaction with respect to ICAM1 was not observed. This result indicated that the extracellular domain of ICAM1 was directed toward the outside of the nanovesicles. In addition, in the case of proteins loaded in the nanovesicles, it can be seen that the proteins are protected by the bilayer membranes of the nanovesicles.

Based on these results, in the case of the nanovesicles prepared using alkaline solution treatment, it was deduced that the extracellular domains of cell membrane proteins other than ICAM1 were directed toward the outside of the nanovesicles as in the originating cells. This indicated that the membranes of the nanovesicles retain the same topology as the cell membranes.

Example 3

Preparation of Nanovesicles Containing Polyethylene Glycol

Nanovesicles containing polyethylene glycol were prepared by loading polyethylene glycol into the monocyte-derived nanovesicles prepared according to the method of Example 1.

After sonication, suspension was performed by adding HBS, and the solution was extruded through a 1 μm filter (two-stack). 0.5 ml of 50% Optiprep, 1 ml of 10% Optiprep, and 3 ml of the suspension were sequentially added into an ultracentrifuge tube, and then ultracentrifugation was performed at 100,000×g for 2 hours to obtain nanovesicles present in the layer between the 50% Optiprep and 10% Optiprep. After ultracentrifugation, 5 μg/ml of cholesterol-polyethylene glycol-biotin was added and incubated at room temperature for 1 hour. Once again, 0.5 ml of 50% Optiprep, 1 ml of 10% Optiprep, and 3 ml of the suspension were sequentially added into a 5 ml ultracentrifuge tube, and then ultracentrifugation was performed at 100,000×g for 2 hours to obtain nanovesicles containing polyethylene glycol present in the layer between the 50% Optiprep and 10% Optiprep.

Next, 10 μg/ml of the nanovesicles containing polyethylene glycol was prepared, 100 μl of the prepared nanovesicles was added to each well of a 96 well plate, and incubated at room temperature for at least 12 hours to coat the wells of the plate. After washing three times with PBS, blocking was performed for 1 hour by adding 100 μl of 1% BSA/PBS. After blocking, the plate was washed three times with PBS, and then streptavidin-HRP was added and incubated for 20 minutes. Thereafter, a BM-POD substrate was added and the amount of color development was measured.

Figure 7:
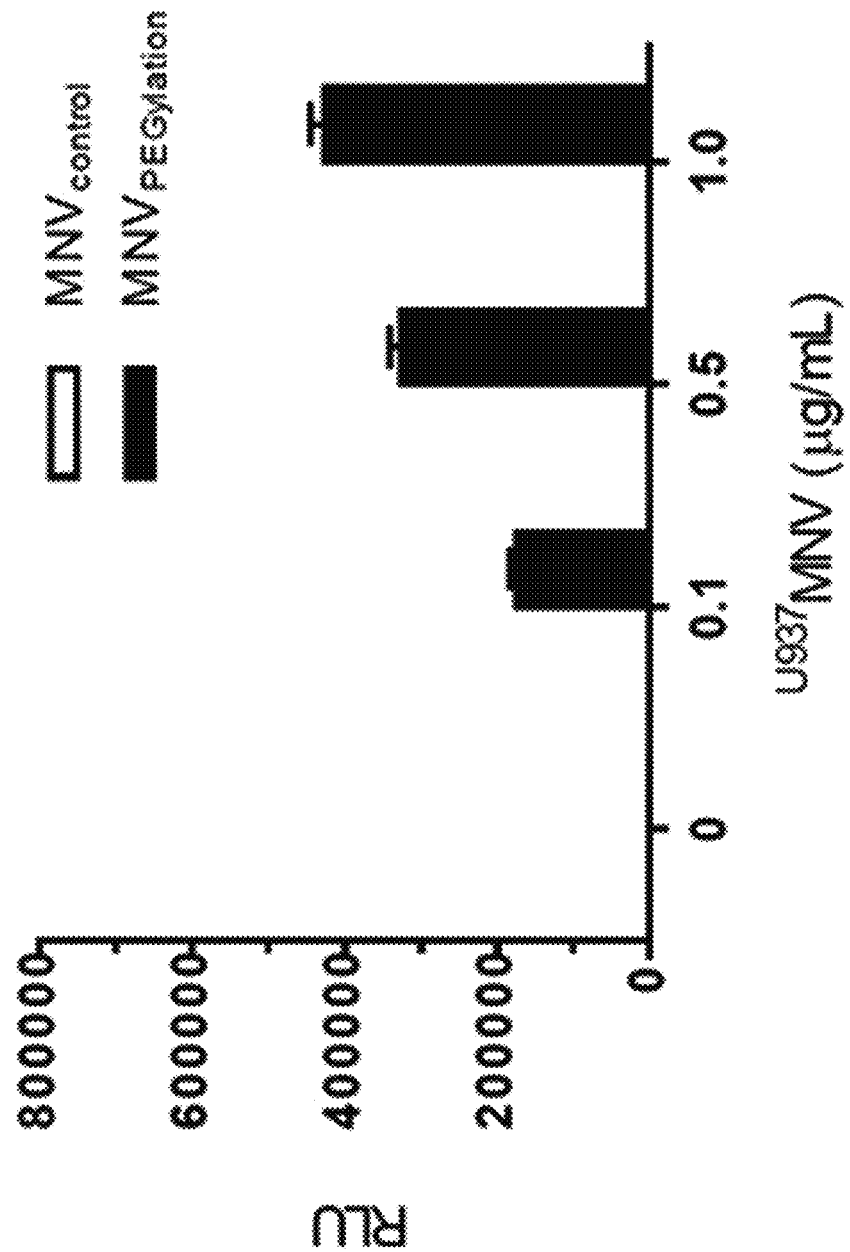
FIG. 7 shows the binding of cholesterol-polyethylene glycol-biotin to the bilayer membranes of nanovesicles derived from nucleated mammalian cells.

As a result, as shown in FIG. 7, when relative luminescence units (RLUs) were measured after color development, the pegylated nanovesicles ($MNV_{PEGylation}$) containing polyethylene glycol exhibited a high RLU value due to the incorporation of cholesterol-polyethylene glycol-biotin into the nanovesicles. On the other hand, nanovesicles ($MNV_{control}$), which had been not treated with cholesterol-polyethylene glycol-biotin, exhibited a low RLU value.

Example 4

Preparation of Nanovesicles Containing FITC-siRNA

To prepare monocyte-derived nanovesicles containing FITC-siRNA, among alkaline solution treatment, sonication, and a density gradient method according to the method of Example 1, in the step of sonication, nanovesicles were loaded with FITC-siRNA.

More specifically, when nanovesicles were prepared from U937 cells, monocytes, as shown in Example 1, the pellet was suspended with 10 ml of a HEPES buffered saline (HBS) solution, ultracentrifugation was performed at 100,000×g for 15 minutes to obtain a pellet. Then, the obtained pellet was suspended with HBS, FITC-siRNA was added to the HBS solution at a concentration of 10 μm to prepare a solution with a final volume of 0.4 ml. Then, sonication was performed 30 times with a sonicator, sonication was performed again for 30 minutes in a water bath sonicator, and the solution was suspended with 0.6 ml of a HBS solution. The solution was extruded through a 1 μm filter (two-stack), and suspended with 2.0 ml HBS. 0.5 ml of 50% Optiprep, 1 ml of 10% Optiprep, and 3 ml of the suspension were sequentially added into a 5 ml ultracentrifuge tube and then ultracentrifugation was performed at 100,000×g for 2 hours to obtain nanovesicles loaded with FITC-siRNA in the layer between the 50% Optiprep and 10% Optiprep.

To verify whether nanovesicles prepared using the method contained FITC-siRNA, 50 μl of the nanovesicles loaded with FITC-siRNA were prepared, and a DiI solution at a concentration of 10 μm was added and the nanovesicles were suspended. The solution was placed on a cover glass, the cover glass was placed in a humid chamber, and stored at 4° C. for at least 12 hours. 5 μl of a mounting solution was loaded on a slide glass, the cover glass was placed thereon, and observation was performed using a fluorescence microscope. The nanovesicles were observed by the red fluorescence of DiI (1,1'-dioctadecyl-3,3,3'3'-tetramethylindocarbocyanine perchlorate), and siRNA was observed by the green fluorescence of FITC. The results are shown in FIG. 8.

Figure 8:
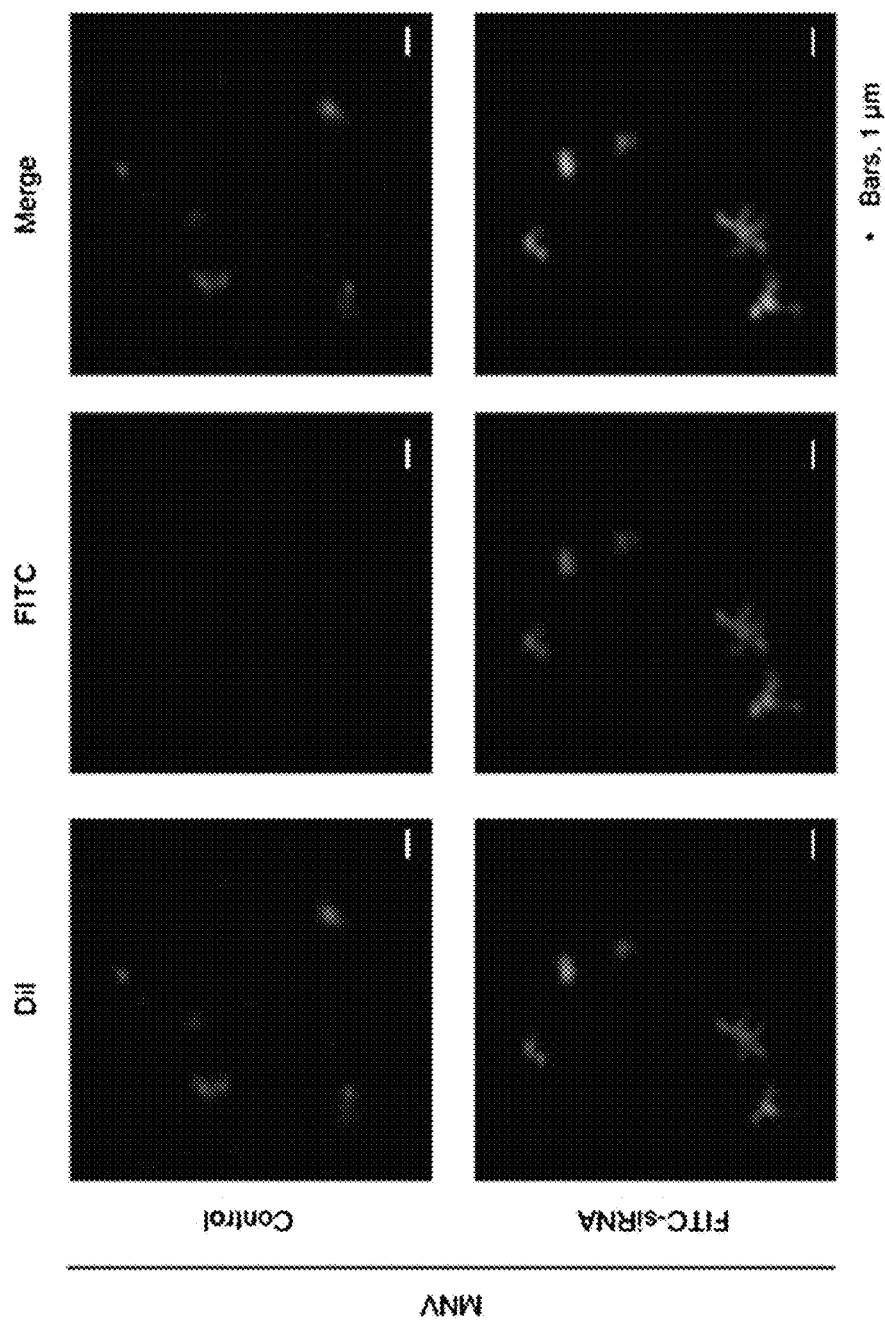
FIG. 8 shows fluorescence microscope images confirming that FITC-siRNA was loaded into nanovesicles derived from nucleated mammalian cells.

As a result, as shown in FIG. 8, nanovesicles not loaded with FITC-siRNA were labeled with DiI and exhibited red fluorescence, but did not exhibit the green fluorescence of FITC-siRNA. On the other hand, nanovesicles loaded with FITC-siRNA exhibited the red fluorescence of DiI as well as the green fluorescence of FITC-siRNA. The presence of green fluorescence and red fluorescence in the same location confirmed that FITC-siRNA was loaded into the nanovesicles.

Example 5

Preparation of Nanovesicles Loaded with Qdot

To prepare nanovesicles loaded with Qdot 705, the same method used in preparation of the FITC-siRNA-loaded nanovesicles of Example 4 was used, and in the step of sonication, 20 nM Qdot 705 was added instead of FITC-siRNA.

To verify whether nanovesicles prepared using the method contained Qdot 705, 50 μl of nanovesicles loaded with 20 μg/ml of Qdot 705 were prepared. Samples were prepared in the same method as Example 4, and observation was performed using a fluorescence microscope. The nanovesicles were observed by the red fluorescence of DiI, and Qdot 705 was observed by a blue pseudo color.

Figure 9:
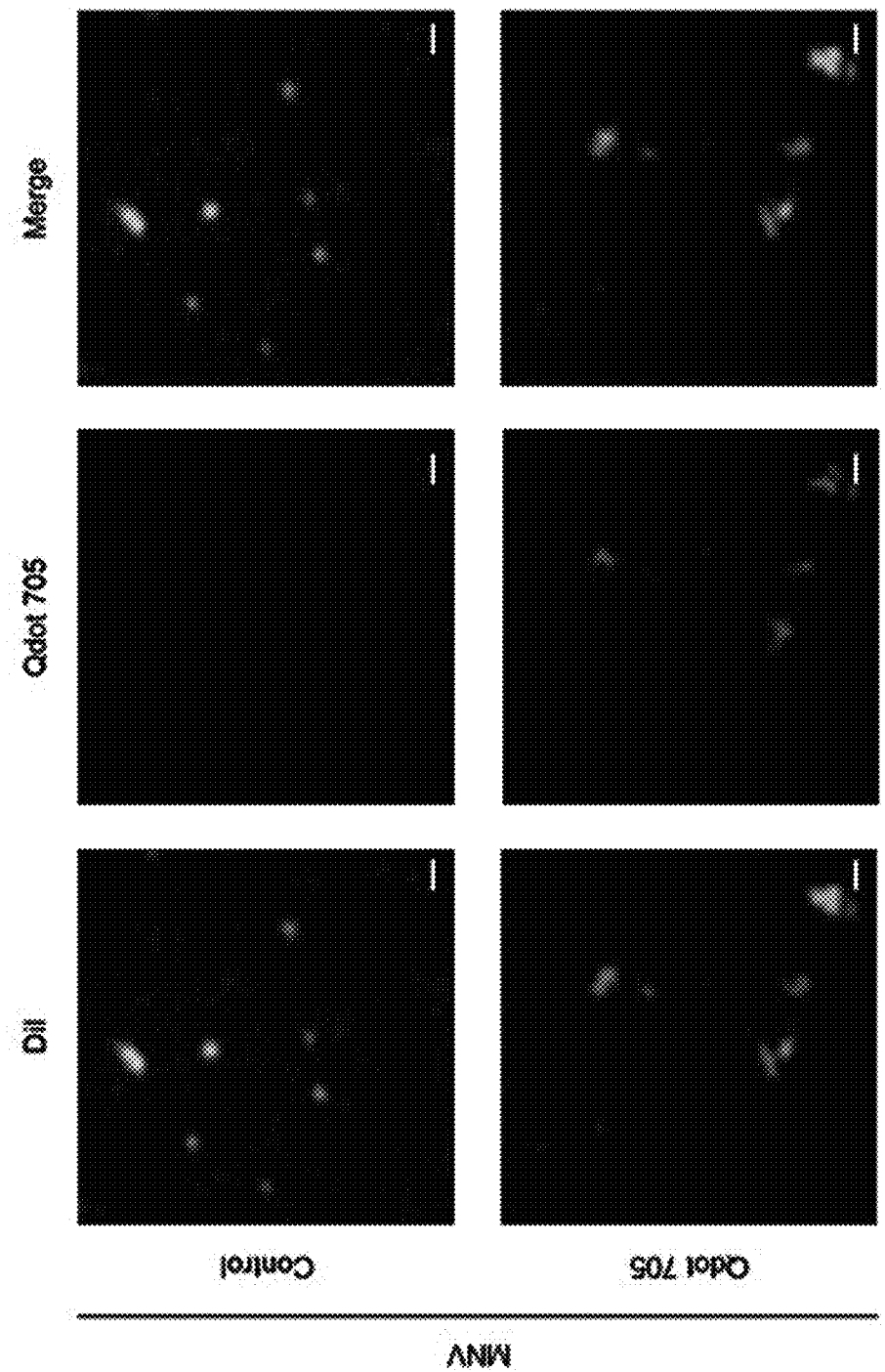
FIG. 9 shows fluorescence microscope images confirming that Qdot 705 was loaded into nanovesicles derived from nucleated mammalian cells.

As a result, as shown in FIG. 9, nanovesicles not loaded with Qdot 705 were labeled with DiI and exhibited red fluorescence, but did not exhibit the blue fluorescence of Qdot 705. On the other hand, nanovesicles loaded with Qdot 705 exhibited the red fluorescence of DiI as well as blue fluorescence. The presence of blue fluorescence and red fluorescence in the same location confirmed that Qdot 705 was loaded into the nanovesicles.

Example 6

Preparation of Nanovesicles Loaded with Iron Oxide Nanoparticles

To prepare nanovesicles loaded with iron oxide nanoparticles, the same method used in preparation of the FITC-siRNA-loaded nanovesicles of Example 4 was used, in the step of sonication, 20 μg/ml of iron oxide nanoparticles was added instead of FITC-siRNA. Then, nanovesicles ($MNV_{iron\ oxide}$) loaded with iron oxide nanoparticles by a density gradient method using an Optiprep solution were compared with nanovesicles ($MNV_{control}$) not loaded with iron oxide nanoparticles.

Figure 10:
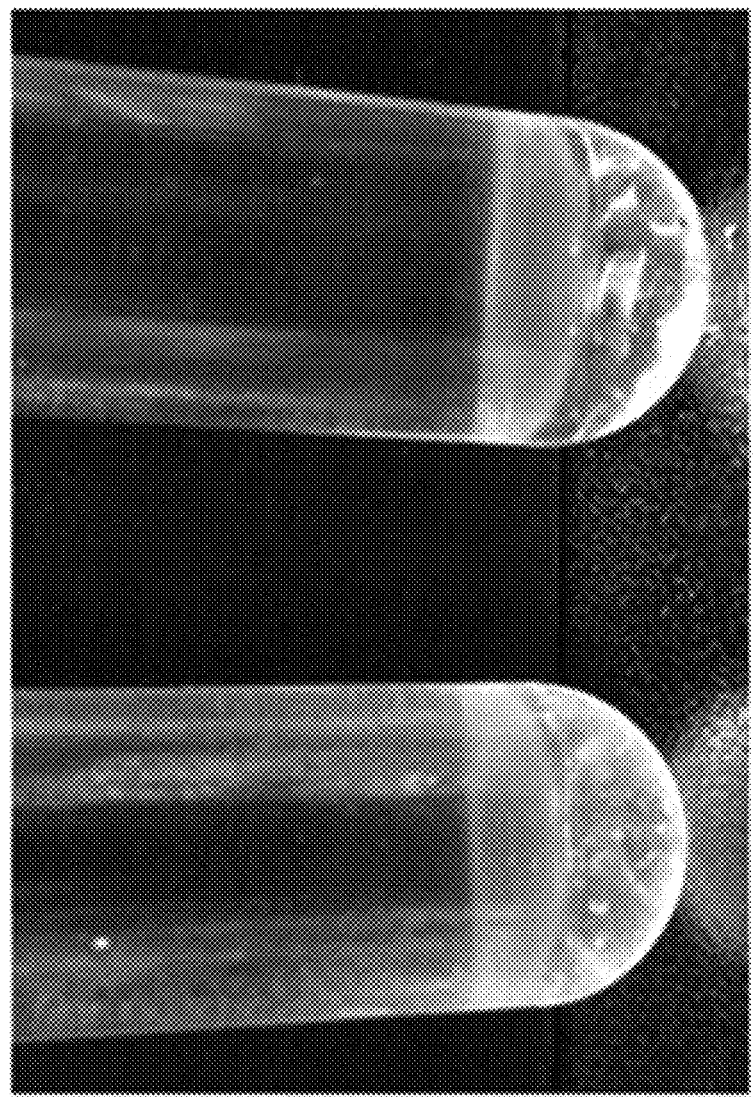
FIG. 10 shows an image confirming that iron oxide nanoparticles were loaded into nanovesicles derived from nucleated mammalian cells. The iron oxide nanoparticles were loaded into the nanovesicles using a density gradient method in an Optiprep solution.

As a result, as shown in FIG. 10, the nanovesicles not loaded with iron oxide nanoparticles exhibited white bands, whereas the nanovesicles loaded with iron oxide nanoparticles exhibited dark brown bands. These results confirmed that iron oxide nanoparticles were loaded into nanovesicles.

Example 7

Validation of Drug Delivery and Cell-Specific Delivery Using Monocyte-Derived Nanovesicles 7-1. Confirmation of In Vitro Chemical Drug Delivery and Cell-Specific Delivery Using Monocyte-Derived Nanovesicles To verify whether the nanovesicles of the present invention deliver chemical drugs in a cell-specific-manner in vitro, monocyte-derived nanovesicles loaded with doxorubicin, an anti-cancer agent, were prepared and a fluorescence microscope was used to verify whether the drug was delivered in a cell-specific manner.

The wells of a 24 well plate were coated with 0.1% gelatin, each well of the plate was seeded with $3 \times 10^4$ of human umbilical vein endothelial cells (HUVECs), and the cells were cultured for 12 hours. An existing culture medium was removed, and a culture medium containing 10 ng/ml of TNF-α was added thereto and cultured for 16 hours. When HUVECs, a human blood vessel cell line, were treated with TNF-α to activate the HUVECs, the expression of cell adhesion molecules such as ICAM-1, VCAM-1, and E-selectin increases in the cell membranes. The increased ICAM-1, VCAM-1, and E-selectin bind to cell adhesion molecules such as LFA-1 and Mac-1 present in monocytes and macrophages. This protein interaction allows monocyte and macrophages to bind to blood endothelial cells.

Accordingly, monocyte-derived nanovesicles loaded with doxorubicin were prepared according to the method of Example 1. In the step of sonication, 800 μg/ml of doxorubicin was added, and sonication was performed to prepare nanovesicles loaded with doxorubicin.

Next, HUVECs were treated with 0, 1, 2, or 5 μg/ml of nanovesicles loaded with doxorubicin for 20 minutes, replaced with a fresh medium, and cultured for 36 hours. After culture, HUVECs were treated with 2 μM CellTracker (CellTracker, Invitrogen. No. C2925), incubated for 1 hour, and then treated with 4% paraformaldehyde for cell fixation. Then, the 4% paraformaldehyde was removed, PBS was added, and a fluorescence microscope was used to observe the cells and measure the number of cells.

Figure 11:
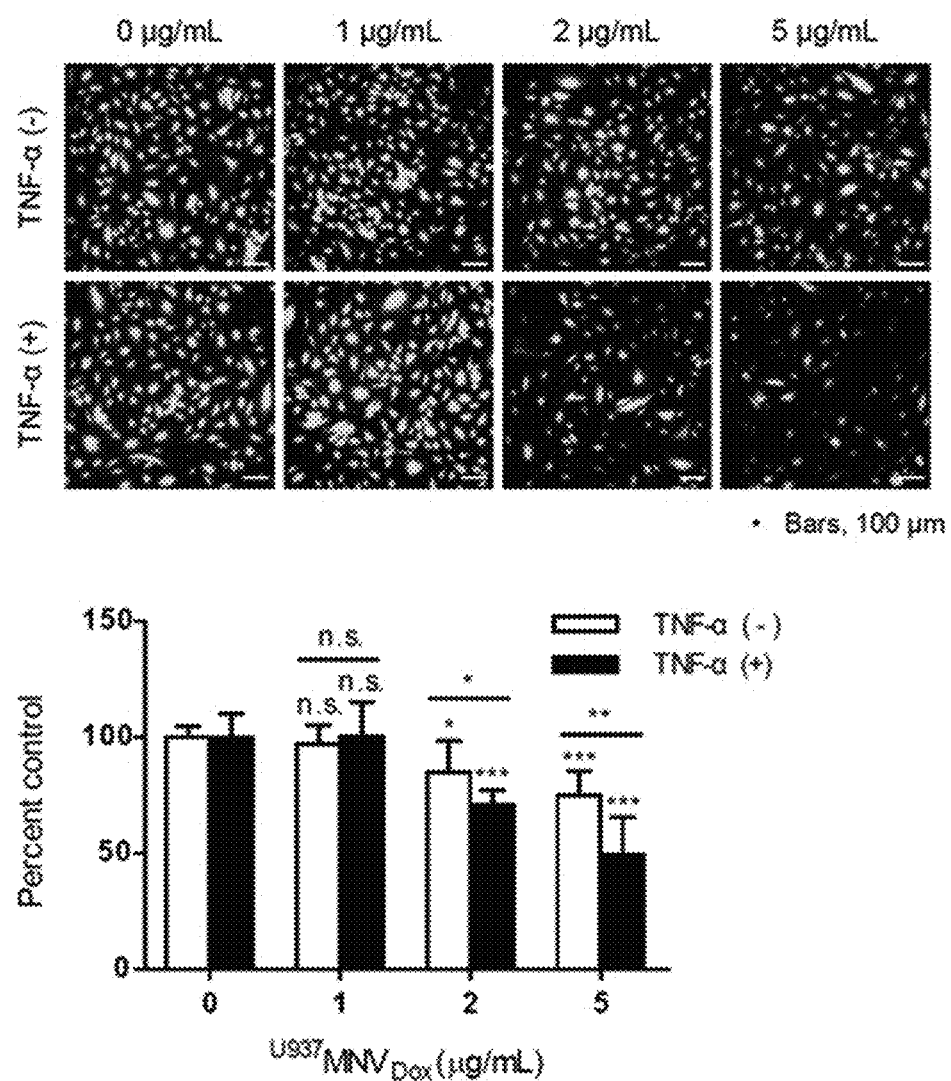
FIG. 11 shows that, under TNF-α treatment conditions, nanovesicles derived from nucleated mammalian cells can be used to deliver doxorubicin into target cells and doxorubicin-induced cell death was increased when the nanovesicles were used.

As a result, as shown in FIG. 11, in the HUVECs without TNF-α treatment, the number of cells decreased to some extent, indicating that nonspecific drug delivery partially occurred. However, when TNF-α was treated at various concentrations, the number of cells significantly decreased depending on the concentration of the nanovesicles. This indicated that more doxorubicin was delivered to HUVECs due to the presence of the nanovesicles. Based on these results, it was confirmed that the nanovesicles may be used to deliver chemical drugs in a cell-specific manner.

7-2. Confirmation of In Vitro Protein Drug Delivery and Cell-Specific Delivery Using Monocyte-Derived Nanovesicles To verify whether the nanovesicles of the present invention deliver protein drugs in a cell-specific-manner in vitro, monocyte-derived nanovesicles loaded with ribonuclease A (RNase A) were prepared and a fluorescence microscope was used to verify whether RNase A was delivered in a cell-specific manner.

Monocyte-derived nanovesicles loaded with RNase A were prepared according to the method of Example 1. In the step of sonication, 800 μg/ml of RNase A was added, and sonication was performed to prepare nanovesicles loaded with RNase A. Samples were prepared by the same principle and method as Example 7-1, and cells were observed under a fluorescence microscope, and then the number of cells was measured.

Figure 12:
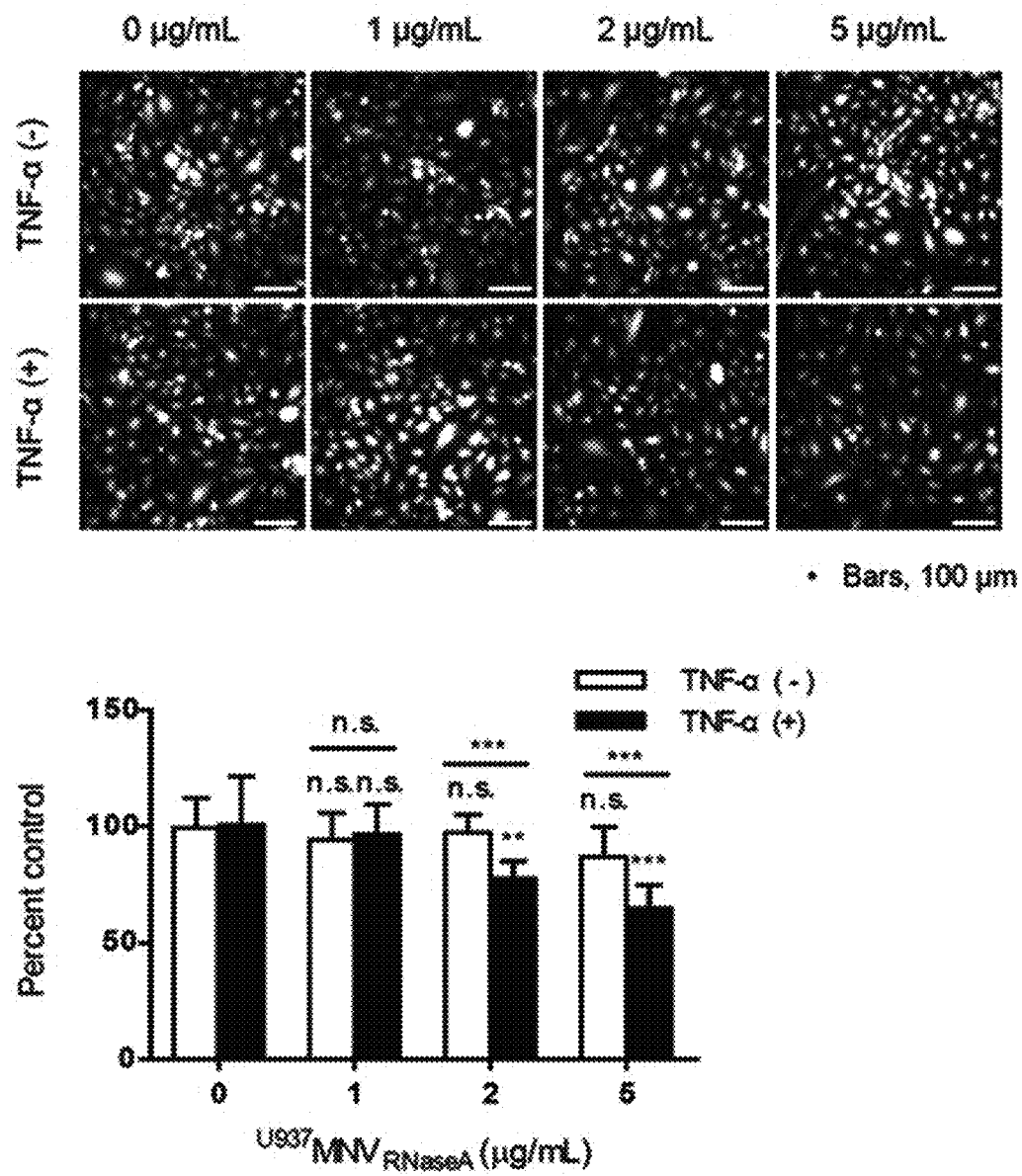
FIG. 12 shows that, under TNF-α treatment conditions, nanovesicles derived from nucleated mammalian cells can be used to deliver ribonuclease A (RNase A) into target cells and ribonuclease A-induced cell death was increased when the nanovesicles were used.

As a result, as shown in FIG. 12, when nanovesicles loaded with RNase A were treated at various concentrations, nonspecific drug delivery was partially observed in HUVECs without TNF-α treatment. However, when TNF-α was treated, the number of cells significantly decreased. This indicated that more RNase A was delivered to HUVECs due to the presence of the nanovesicles. Based on these results, it was confirmed that the nanovesicles may be used to deliver protein drugs in a cell-specific manner.

Example 8

Validation of In Vitro Drug Delivery Using Transformed Cell-Derived Nanovesicles To verify whether the nanovesicles prepared from transformed cells deliver drugs in a cell-specific manner like the monocyte-derived nanovesicles of Example 7, monocyte-derived nanovesicles loaded with doxorubicin, an anticancer agent, or RNase A were prepared. Monocyte cells were treated with the prepared nanovesicles, and then the number of living cells was measured.

Nanovesicles, which were derived from HT1080 transformed cells expressing ICAM-1 and loaded with doxorubicin or RNase A, were prepared according to the method of Example 1. In the step of sonication, 800 μg/ml of doxorubicin or RNase A was added, and sonication was performed to prepare nanovesicles loaded with doxorubicin or RNase A.

Thereafter, 500 μl of a medium containing $1 \times 10^5$ U937 cells, monocytes, was added to each well of a 24 well plate, and 0, 1, 2, 5, or 10 μg/ml of HT1080 cell-derived nanovesicles was added thereto, followed by incubation for 24 hours. After incubation, 50 μl of a solution containing the cells was added to each well of a 96 well plate, and each well was treated with 50 μl of a trypan blue solution. In living cells, trypan blue is secreted out of the cells again, so the cells are not stained with trypan blue. 10 μl of the mixed solution was added to a hemocytometer, and the number of cells not stained with trypan blue was measured under an optical microscope.

Figure 13:
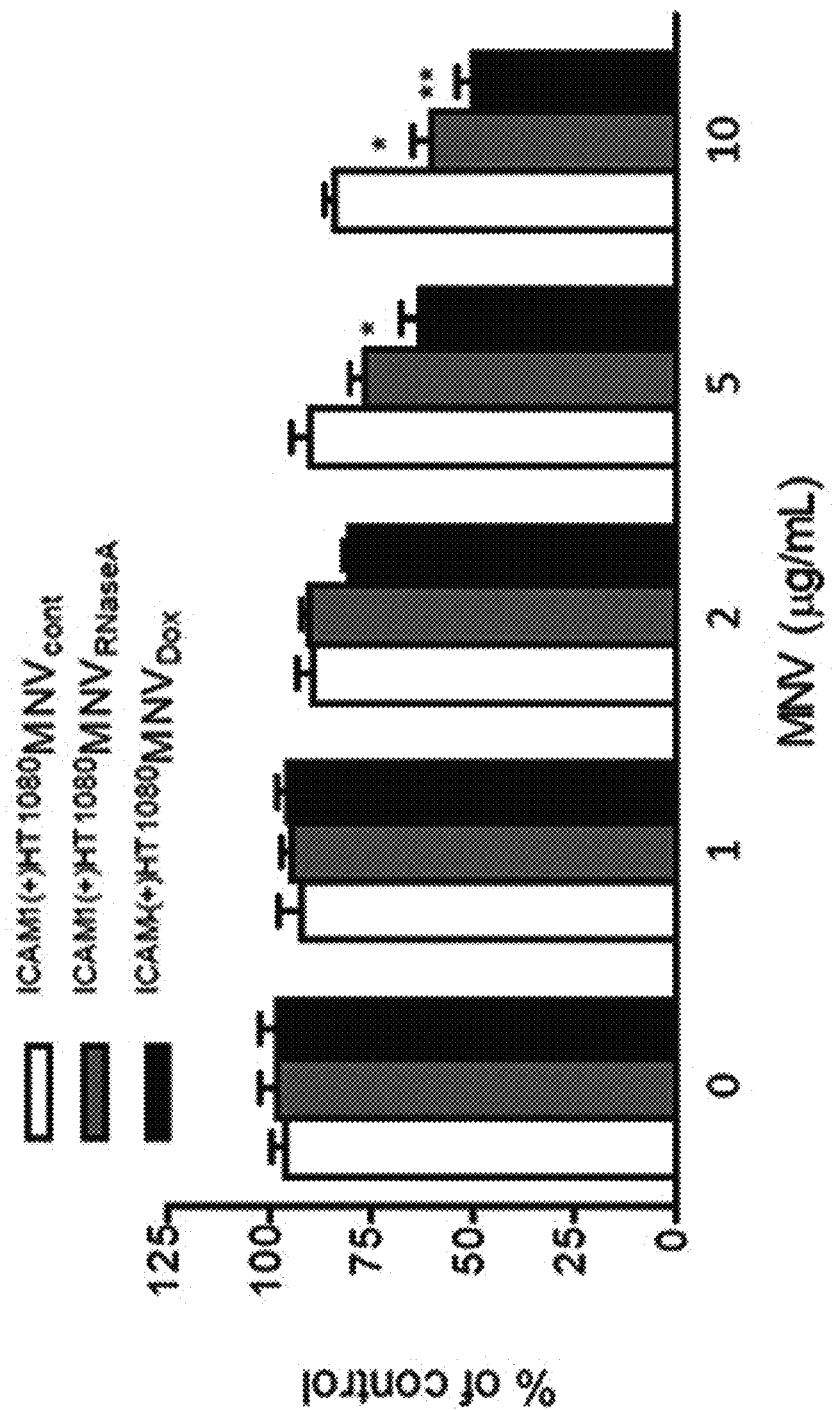
FIG. 13 shows that nanovesicles derived from transformed nucleated cells can be used to deliver doxorubicin or RNase A into the specific types of cells and doxorubicin- or RNase A-induced cell death was increased when the nanovesicles were used.

As a result, as shown in FIG. 13, nanovesicles prepared from transformed HT1080 cells expressing ICAM-1 were not loaded with drugs or loaded with drugs, and two types of nanovesicles were compared. In the case of nanovesicles not loaded with drugs, cell death was not induced by treatment with a high concentration of nanovesicles. On the other hand, when doxorubicin-loaded nanovesicles were treated, cell death was induced from 5 μg/ml. In the case of RNase A-loaded nanovesicles, cell death was induced from 10 μg/ml.

Example 9

Validation of In Vitro Drug Delivery and Cell-Specific Delivery Using Nanovesicles Derived from Transformed Cells Expressing GE11 and EGF in Cell Membranes Each well of a 12 well plate was seeded with $5 \times 10^4$ A549 cells, a human lung cancer cell line, expressing EGFR, and the cells were cultured for 16 hours. EGFR present in A549 is capable of binding to adhesion molecules such as EGF and GE11.

The plate seeded with the A549 cells was washed with PBS, and 1 ml of a medium was added to each well of the plate. Then, $0.1 \times 10^9$, $1 \times 10^9$, or $10 \times 10^9$ particles/ml of nanovesicles, which had been prepared from transformed cells expressing EGF and GE11 in the membranes according to Example 1 and loaded with doxorubicin, were added to each well of the plate, followed by incubation for 20 minutes. After incubation, each well was washed with PBS, 1 ml of a medium was added thereto, and cultured for 36 hours. Then, after PBS washing, 500 μl of a serum free medium was added to each well, 5 µM CellTracker (Invitrogen. No. C2925) was added thereto, and incubated for 30 minutes. Thereafter, 500 µl of 4% paraformaldehyde was added to each well, incubated for 10 minutes for cell fixation, and the fixed cells were observed under a fluorescence microscope.

Figure 14:
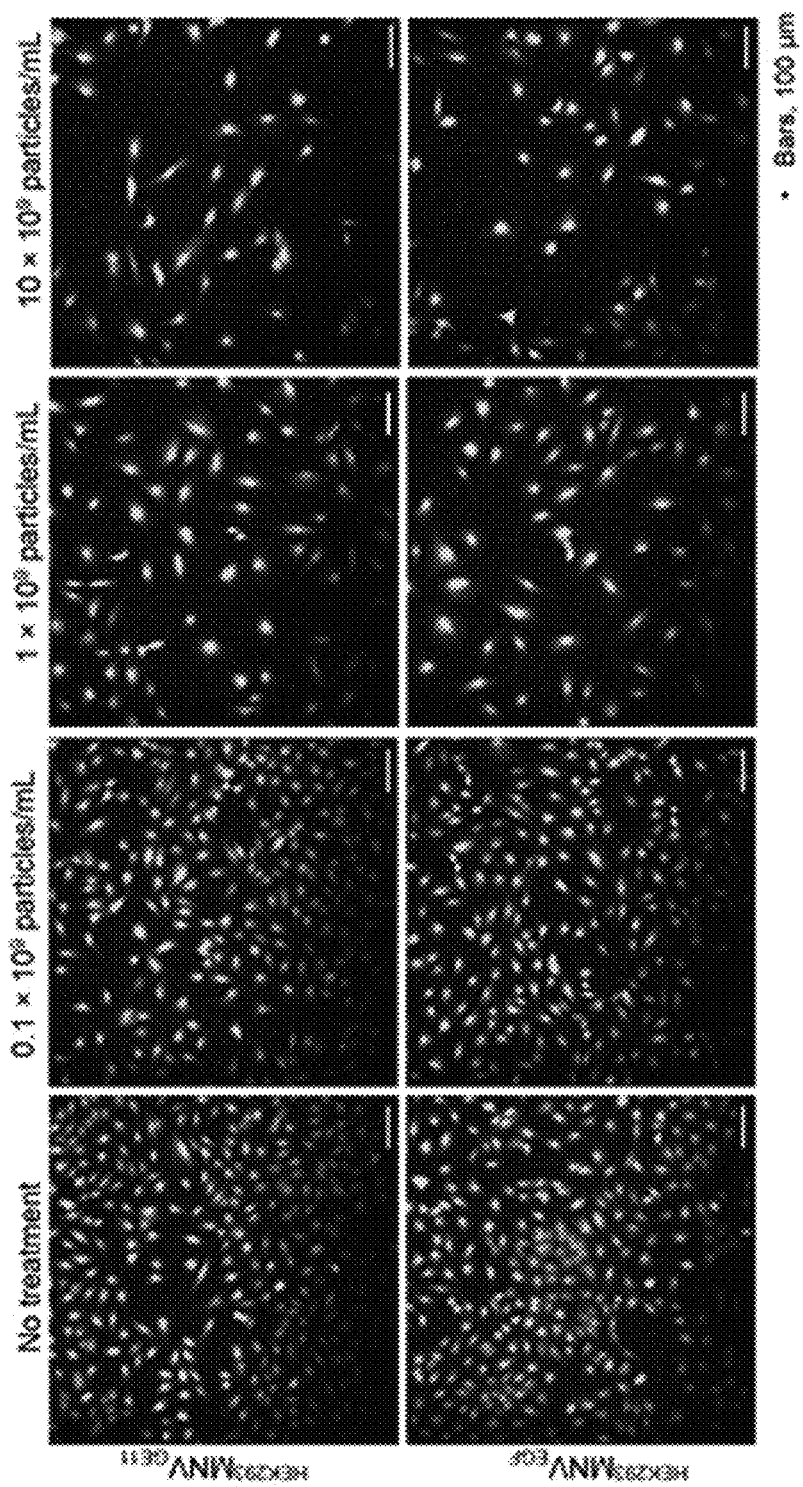
FIG. 14 shows that nanovesicles derived from transformed nucleated cells can be used to specifically deliver doxorubicin into human lung cancer cells and doxorubicin-induced cell death was increased when the nanovesicles were used.

As a result, as shown in FIG. 14, it was confirmed that the number of living cells decreased as the concentration increased. In conclusion, nanovesicles, which had been derived from transformed cells expressing EGF and GE11 in the cell membranes and loaded with anticancer drugs, were capable of binding to cells expressing EGFR on the cell surface, and consequently, the loaded anticancer drugs were selectively delivered to the EGFR expressing cells, resulting in cell death.

The aforementioned description of the present invention is provided by way of example and those skilled in the art will understood that the present invention can be easily changed or modified into other specified forms without change or modification of the technical spirit or essential characteristics of the present invention. Therefore, it should be understood that the aforementioned examples are only provided by way of example and not provided to limit the present invention.

The invention claimed is:

1. Nanovesicles prepared from membranes of cells,
   wherein intracellular components including genetic materials and cytosolic proteins are removed in the nanovesicles by treating the cells with an alkaline solution of pH 9 to 14 and sonication of the treated cells, and the size of the nanovesicles is smaller than the size of the cells,
   wherein the nanovesicles are loaded with one or more substances for treating or diagnosing a disease selected from the group consisting of an anti-cancer agent, an anti-inflammatory agent, an angiogenesis inhibitor, a toxin, a bead, a microparticle, a nanoparticle, and a fluorescence-emitting material, and
   wherein the nanovesicles retain topology of membrane proteins of the cells from which the nanovesicles originate.

2. The nanovesicles according to claim 1, wherein the cells are capable of targeting specific types of cells or tissues.

3. The nanovesicles according to claim 1, wherein the cells are genetically transformed to express one or more selected from the group consisting of cell adhesion molecules, antibodies, targeting proteins, cell membrane fusion proteins, and fusion proteins thereof.

4. The nanovesicles according to claim 1, wherein the cells are genetically transformed to express one or more selected from the group consisting of growth factors, cytokines, receptors, fluorescent proteins, and fusion proteins thereof.

5. The nanovesicles according to claim 1, wherein membranes of the nanovesicles further comprises non-cellular membrane components,
   wherein the noncellular membrane components are selected from the group consisting of cyclodextrin, polyethylene glycol, and chemically modified membrane components thereof.

* * * * *